US00PP28274P2

(12) United States Plant Patent
Nir

(10) Patent No.: US PP28,274 P2
(45) Date of Patent: Aug. 15, 2017

(54) ***CHAMELAUCIUM* PLANT NAMED 'LUNA'**

(50) Latin Name: *Chamelaucium uncinatum*
Varietal Denomination: LUNA

(71) Applicant: Nitzan Nir, Kfar Hess (IL)

(72) Inventor: Nitzan Nir, Kfar Hess (IL)

( * ) Notice: Subject to any disclaimer, the term of this patent is extended or adjusted under 35 U.S.C. 154(b) by 0 days.

(21) Appl. No.: 14/999,345

(22) Filed: Apr. 25, 2016

(51) Int. Cl.
*A01H 5/02* (2006.01)

(52) U.S. Cl.
USPC ..... Plt./229

(58) Field of Classification Search
USPC ..... Plt./229
See application file for complete search history.

*Primary Examiner* — Annette Para
(74) *Attorney, Agent, or Firm* — Cassandra Bright

(57) ABSTRACT

A new and distinct *Chamelaucium* cultivar named 'LUNA' is disclosed, characterized by small white flowers with uniquely semi-erect petals. Flower production begins in mid-December and continues until March. The new variety is a *Chamelaucium*, normally producing cut flower stems, or as a garden or container plant.

1 Drawing Sheet

Latin name of the genus and species: *Chamelaucium uncinatum.*

Variety denomination: 'LUNA'.

BACKGROUND OF THE INVENTION

The new *Chamelaucium* cultivar is the product of a planned breeding program conducted by the inventor, Nitzan Nir, in Kfar Hess, Israel. The objective of the breeding program was to produce new *Chamelaucium* varieties for ornamental commercial applications. The new variety was selected as a seedling from the breeding program at a commercial nursery in Kfar Hess, Israel.

The crossing resulting in this new variety was made in February of 2010. The seed parent is the unpatented proprietary variety referred to as *Chamelaucium uncinatum* '95.1'. The pollen parent is the unpatented, variety referred to as *Chamelaucium uncinatum* 'Atar L'. The new variety was discovered in December of 2011 by the inventor in a group of seedlings resulting from previously mentioned crossing, in a commercial nursery in Kfar Hess, Israel.

Asexual reproduction of the new cultivar has been performed by terminal vegetative cuttings. This was first performed at a commercial nursery in Kfar Hess, Israel in March of 2011 and has shown that the unique features of this cultivar are stable and reproduced true to type in at least 4 successive generations.

SUMMARY OF THE INVENTION

The cultivar 'LUNA' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LUNA'. These characteristics in combination distinguish 'LUNA' as a new and distinct *Chamelaucium* cultivar:

1. Blooming season from mid-December until March, in Kfar Hess, Israel.

2. Unique semi-erect flower petal attitude.
3. Small flower size.
4. White flowers.

PARENT COMPARISON

Plants of the new cultivar 'LUNA' are similar to plants of the seed parent in most horticultural characteristics, however, plants of the new cultivar 'LUNA' differ in the following:

1. Bloom time of the new variety is Mid-December until March, the seed parent '95.1' blooms from Mid-February until March.
2. Flower petals of the new variety are semi-erect, flower petals of the seed parent are horizontal.

Plants of the new cultivar 'LUNA' are similar to plants of the pollen parent; in most horticultural characteristics, however, plants of the new cultivar 'LUNA' differ in the following:

1. Bloom time of the new variety is Mid-December until March, the pollen parent blooms from January until March.
2. Flower petals of the new variety are semi-erect, flower petals of the pollen parent are horizontal.

COMMERCIAL COMPARISON

Plants of the new cultivar 'LUNA' are comparable to the variety *Chamelaucium uncinatum* 'Atar E.', unpatented. The two *Chamelaucium* varieties are similar in most horticultural characteristics; however, the new variety 'LUNA' differs in the following:

1. Bloom time of the new variety is Mid-December until March, this comparator variety blooms from January until March.
2. Flower petals of the new variety are semi-erect, flower petals of this comparator are horizontal.

Plants of the new cultivar 'LUNA' can also be compared to the commercial variety *Chamelaucium uncinatum* 'Early Ofir', U.S. Plant Pat. No. 26,023. These varieties are similar in most horticultural characteristics however, the new variety 'LUNA' differs in the following:

1. Bloom time of the new variety is Mid-December until March, this comparator variety blooms from December until February.
2. Flower petals of the new variety are semi-erect, flower petals of this comparator are horizontal.
3. The new variety produces a smaller flower than this comparator.

BRIEF DESCRIPTION OF THE PHOTOGRAPH

The accompanying photograph illustrates in full color a close up of typical flowers and foliage of 'LUNA' at approximately 1 year of age. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'LUNA' plants grown outdoors in Kfar Hess, Israel. The growing temperature ranged from 15° C. to 35° C. during the day and from −2° C. to 35° C. during the night. General light conditions are bright, normal sunlight. Measurements and numerical values represent averages of typical plant types.

Botanical classification: *Chamelaucium uncinatum* 'LUNA'.

Age of plant described: At least 2 months old from a rooted cutting.

Typical flowering stems harvested per plant: 120 to 150 during the course of the season.

Vase life of flowers: Two weeks.

PROPAGATION

Time to produce a rooted plantlet: 30 to 60 days at approximately 24° C.

Root description: Fibrous. Greyed-Brown in color, not accurately measured with RHS chart.

PLANT

Growth habit: Upright plant produces multiple stems from a pinch, or after harvesting stems.

Height: 200 cm.

Plant spread: 80 cm.

Growth rate: Rapid.

Branching characteristics: Moderate to high branching occurs after pinching.

Length of primary lateral branches: 60 cm to 90 cm on average.

Diameter of lateral branches: 0.1 to 0.2 cm.

Quantity of primary lateral branches: 120 to 150, these are the harvested flowering stems.

Characteristics of primary lateral branches:

*Form*.—Round.

*Diameter*.—0.5 cm, measured at 50 cm from top.

*Color*.—Near RHS Grey-Green 197A.

*Texture*.—Smooth.

*Strength*.—Stems somewhat brittle.

Internode length: Range from 2.0 to 9.0 cm.

FOLIAGE

Leaf:

*Arrangement*.—Opposite.

*Quantity*.—Approximately 8 leaves, in the 5-10 cm section from the top of the branch.

*Average length*.—2.0 cm.

*Average width*.—0.1 cm.

*Shape of blade*.—Needle

*Apex*.—Acute.

*Base*.—Attenuate.

*Margin*.—Entire.

*Texture*.—Glabrous all surfaces.

*Pubescence*.—None.

*Aspect*.—Straight, occurring at approximately a 15 to 30 degree angle.

*Color*.—Young foliage: Near RHS Green 137A. Mature foliage: Near RHS Green 137A.

*Venation*.—Indistinguishable from foliage.

*Petiole*.—Not present.

FLOWER

Natural flowering season: Flowering Begins mid-December and continues until March, without a juvenility period in Kfar Hess, Israel. Plants flower continuously under short day conditions.

Days to flowering from rooted cutting: Approximately 45 to 70 days.

Inflorescence type: Terminal Panicle.

Individual flower type: Single, rotate 5 petaled with a cone shaped hypanthium. Flowers outwardly and upwardly facing.

Persistent or self-cleaning: Self-Cleaning.

Lastingness: About 2 weeks in a vase. Approximately 45 to 70 days on the plant.

Typical flowering stem length: Approximately 60 to 80 cm.

Bud:

*Shape*.—Flattened sphere.

*Length*.—0.5 cm.

*Diameter*.—0.3 to 0.4 cm.

*Color*.—Near RHS Yellow-Green 151D.

Inflorescence size:

*Diameter*.—Average 20 to 25 cm.

*Length*.—Average 30 to 40 cm.

Flower size:

*Diameter*.—Average 1.5 cm.

*Length*.—Average 1.0 cm.

Corolla:

*Petals*.—Arrangement: Rotate, not overlapping. Length: Average 0.6 cm. Diameter: Average 0.5 cm. Quantity: 5. Attitude: Semi-Erect. Texture: Smooth. Apex: Obtuse rounded. Base: Fused into a hypanthium.

*Color*.—When opening: Upper surface: Near RHS White N155A. Lower surface: Near RHS White N155A. Fully opened: Upper surface: Near RHS White N155A. Lower surface: Near RHS White N155A. Aging: Upper surface: Near RHS White N155A. Lower surface: Near RHS White N155A.

*Interior corolla/tube*.—Diameter: 0.5 cm. Length: 0.25 cm.

*Color*.—When opening: Upper surface: Near RHS Yellow-Green 144A. Lower surface: Near RHS Yellow-Green 153C. Fully opened: Upper surface: Near RHS Yellow-Green 152B. Lower surface: Near RHS Greyed-Yellow 160B. Aging: Upper surface: Near RHS Yellow-Green 146C. Lower surface: Near RHS Yellow-Green 152D.

Hypanthium:

*Diameter*.—Average 0.4 cm.

*Length*.—Average 0.2 cm.

*Shape*.—Obconical.

*Color*.—When opening: Inner surface: Near RHS Yellow-Green 144C. Outer surface: Near RHS Yellow-Green 144B. Fully opened: Inner surface: Near RHS Yellow-Green 146C. Outer surface: Near RHS Yellow-Green 151D. Aging: Inner surface: Near RHS Yellow-Green 146C. Outer surface: Near RHS Yellow-Green 151D.

Calyx/sepals:

*Quantity per flower*.—Fused into a single, conical structure.

*Length*.—0.25 cm.

*Width*.—0.5 cm.

*Margin*.—Entire.

*Texture*.—Smooth.

*Color*.—Near RHS Yellow-Green 144A, center section near Yellow-green 151D.

Peduncle: Peduncle consists of the plant stem.

Pedicel:

*Length*.—0.8 to 0.9 cm.

*Diameter*.—0.05 cm.

*Color*.—Near RHS Yellow Green 144A.

Fragrance: None.

REPRODUCTIVE ORGANS

Stamens:

*Number*.—10.

*Filament length*.—1 mm.

*Filament color*.—Near RHS Yellow-Green 154D.

Anthers:

*Shape*.—Oval.

*Length*.—0.25 mm.

*Width*.—0.2 mm.

*Color*.—Near RHS Greyed-Yellow 160B.

Pollen: Not observed.

Pistil:

*Number*.—1. Style Length: 0.4 cm. Style color: Near RHS White 155C.

*Stigma*.—Shape: Round. Color: Near RHS Greyed-Yellow 160B. Texture: Glabrous.

OTHER CHARACTERISTICS

Seeds and fruits: Single flower produces one fruit. When the fruit is fertile, it will produce 1 seed, occasionally 2 seeds. Fruit type is a nut, colored near Grey-Brown N199A, seed is unwinged colored approximately 1 mm, brown in color, too minute to accurately measure color with RHS chart.

Disease/pest resistance: Neither resistance nor susceptibility to the normal diseases and pests of *Chamelaucium* have been observed to date.

Temperature tolerance: From —2° C. to 35° C.

Drought tolerance: Very good tolerance for drought.

What is claimed is:

1. A new and distinct cultivar of *Chamelaucium* plant named 'LUNA' as herein illustrated and described.

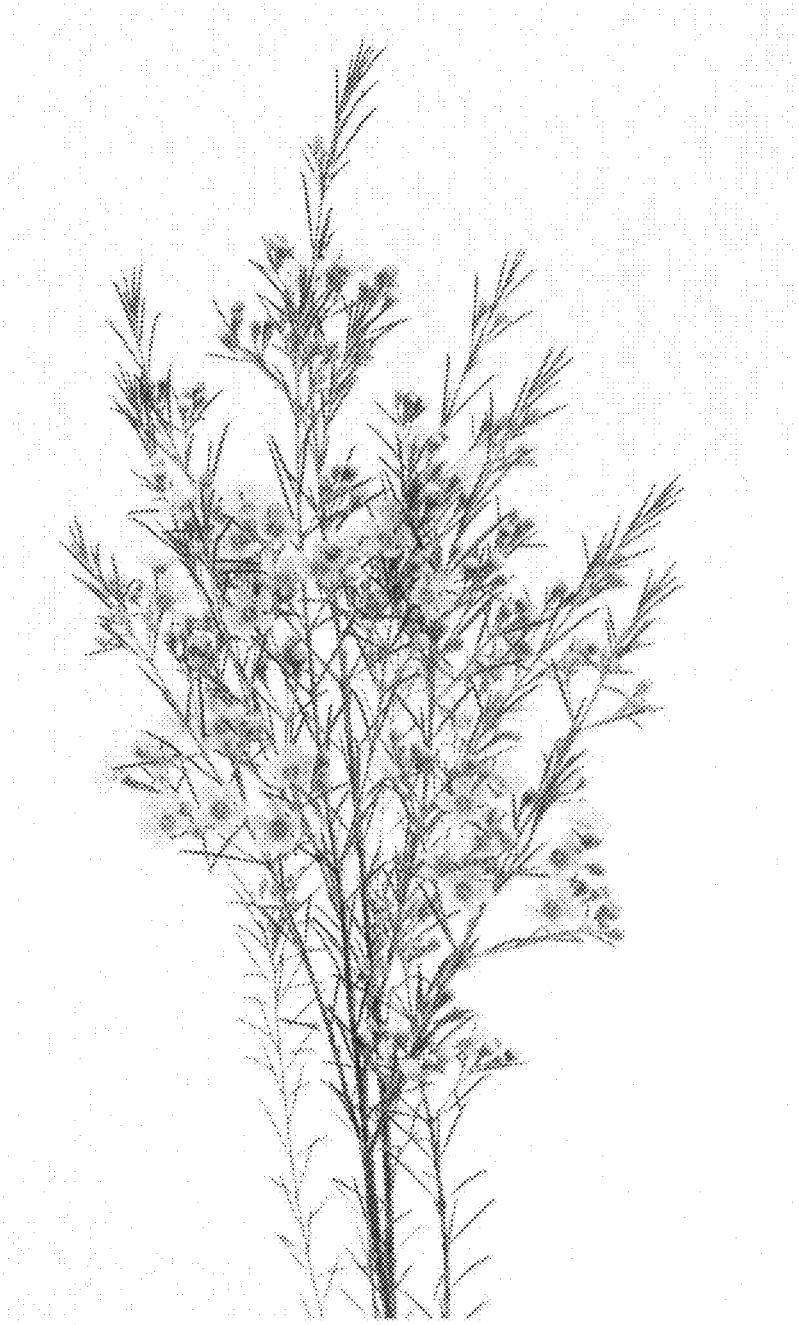

* * * * *